US 6,794,789 B2
(12) United States Patent
Siess et al.

(10) Patent No.: US 6,794,789 B2
(45) Date of Patent: Sep. 21, 2004

(54) MINIATURE MOTOR

(75) Inventors: Thorsten Siess, Wuerselen (DE); Gebhard Doepper, Wolpertshausen (DE)

(73) Assignee: Impella CardioSystems AG (DE)

( * ) Notice: Subject to any disclaimer, the term of this patent is extended or adjusted under 35 U.S.C. 154(b) by 0 days.

(21) Appl. No.: 10/432,470

(22) PCT Filed: Nov. 6, 2001

(86) PCT No.: PCT/EP01/12817

§ 371 (c)(1),
(2), (4) Date: May 22, 2003

(87) PCT Pub. No.: WO02/41935

PCT Pub. Date: May 30, 2002

(65) Prior Publication Data

US 2004/0046466 A1 Mar. 11, 2004

(30) Foreign Application Priority Data

Nov. 25, 2000 (DE) .......................... 100 58 669

(51) Int. Cl.⁷ ............................... H02K 1/12
(52) U.S. Cl. ............................... 310/259; 310/40 MM; 310/216
(58) Field of Search ............................... 310/254, 258, 310/259, 216–218, 40 MM

(56) References Cited

U.S. PATENT DOCUMENTS

| | | | |
|---|---|---|---|
| 3,680,671 A | * 8/1972 | Hendershot et al. | ....... 192/21.5 |
| 4,347,457 A | * 8/1982 | Sakamoto | .................... 310/256 |
| 4,482,829 A | 11/1984 | Tardiue et al. | ............... 310/105 |
| 4,679,313 A | 7/1987 | Schultz et al. | ................ 29/596 |
| 4,968,911 A | * 11/1990 | Denk | .......................... 310/42 |
| 5,142,178 A | * 8/1992 | Kloster et al. | .............. 310/217 |
| 5,689,147 A | * 11/1997 | Kaneda et al. | .............. 310/216 |
| 5,692,882 A | * 12/1997 | Bozeman et al. | ............. 417/45 |
| 5,698,925 A | * 12/1997 | Coupart | ...................... 310/217 |
| 5,911,685 A | 6/1999 | Siess et al. | .................. 600/16 |

FOREIGN PATENT DOCUMENTS

| | | |
|---|---|---|
| DE | 198 21 307 C1 | 5/1998 |
| EP | 0 764 448 A2 | 3/1997 |
| WO | WO 98/44619 A1 | 10/1998 |

* cited by examiner

Primary Examiner—Dang Le
(74) Attorney, Agent, or Firm—Fulwider Patton Lee & Utecht, LLP

(57) ABSTRACT

The micromotor serves to drive an impeller (12) rotating in a pump housing (14). The excitation winding of the micromotor is surrounded by an enveloping flux return structure (18) of ferromagnetic material divided into rings (35). The rings (35) are separated from each other by slots (25). The slots are produced by laser cutting of a continuous tube. The enveloping flux return structure has a small wall thickness of a few tenths of a millimeter. The rings (35) are mutually connected by bridges (26). The enveloping flux return structure (18) can be integrally formed with the pump housing (14) of the pump (11). The micromotor can be produced in a small format with a small diameter. It has a high flow rate at a correspondingly high rotational speed. The micromotor is particularly suitable for introducing blood pumps into the vascular system in a non-operative minimally invasive percutaneous manner.

13 Claims, 2 Drawing Sheets

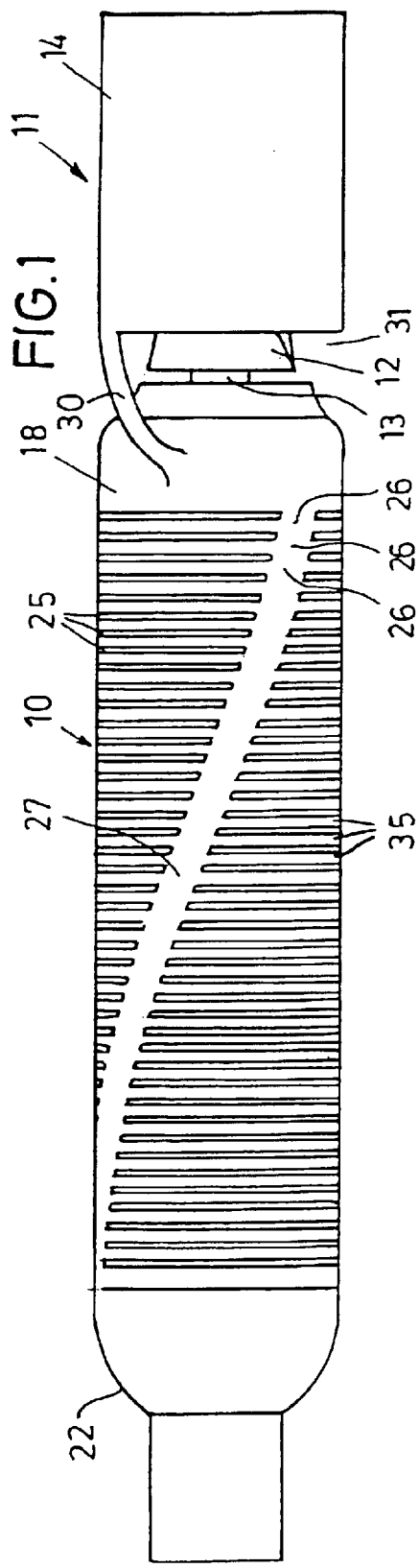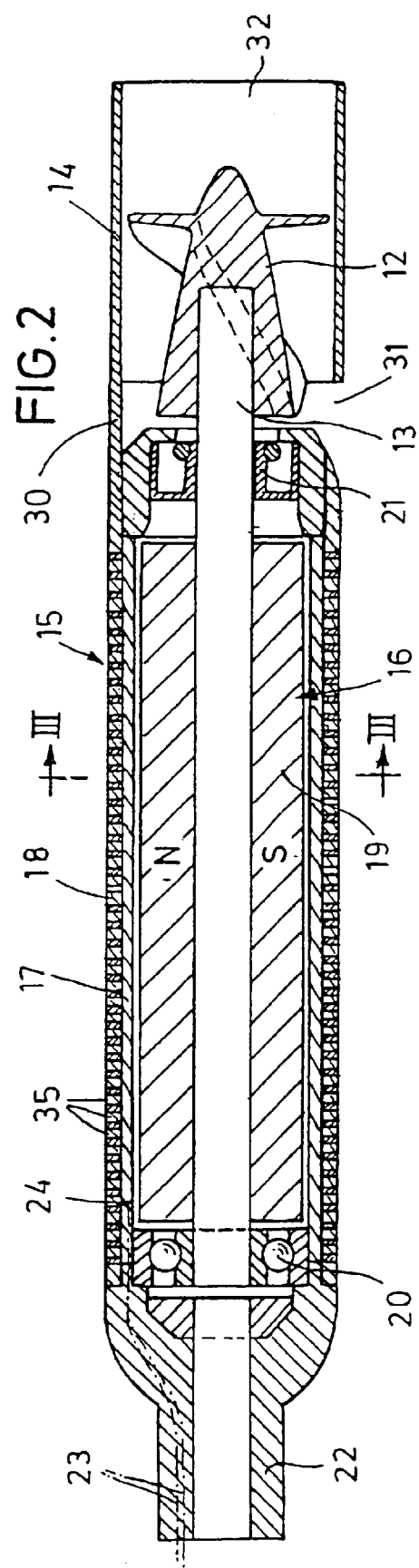

MINIATURE MOTOR

The invention relates to a micromotor with a stator comprising a sleeve with an excitation winding and an enveloping flux return structure of spaced ferromagnetic rings, and particularly a micromotor combined with a pump portion and forming an impeller pump.

In the field of medical technique, blood pumps are needed which are introduced into the body of a patient and placed in an artery or the heart to support the heart function. An intracardiac blood pump provided for operation in the heart is described in DE 198 21 307. The blood pump comprises a drive portion wilth an electric micromotor and a pump portion. It has a maximum outer diameter of about 8 mm and a rigid length of less than 35 mm. The small-scale blood pump having the required flow rate requires a high rotational pump speed of at least 30,000 revolutions per minute, typically of 60,000 revolutions per minute.

A micromotor suitable for the operation of a blood pump is described in WO 98/44619. This micromotor has a stator and a permanently magnetized rotor. The stator includes an excitation winding surrounded by an enveloping flux return structure. The enveloping flux return structure bundles the magnetic field lines generated by the excitation winding and concentrates them so that only little magnetic flux is lost by stray fields. The enveloping flux return structure consists of pieces of sheet metal which are electrically insulated with respect to each other and assembled to a tubular stack.

The wish to introduce pumps with a catheter into the vascular system of a patient by punction without being forced to operatively open the patient body results in the need of ever smaller pumps and motors the diameters of which are in the range of 4 mm. With such small dimensions, there is only very little room available for the enveloping flux return structure in the case of an electric micromotor. Here, the enveloping flux return structure can only have a wall thickness of a few tenths of a millimeter. An enveloping flux return structure of such a small wall thickness cannot be assembled from pieces of sheet metal. On the other hand, an enveloping flux return structure is useful in order to avoid a loss of energy by magnetic field leakage.

It is the object of the invention to provide a micromotor with high efficiency and small radial dimensions. This object is solved, according to the invention, with the features indicated in claim 1. Accordingly, the enveloping flux return structure consists of an integral body wherein adjacent rings are connected by at least one bridge. This means that the enveloping flux return structure is made of an integral tube, and the rings are not completely electrically insulated with respect to each other as is the case with sheet metal pieces. They are rather interconnected, on the one hand, and spaced, on the other hand, by the bridges. It is required to divide the enveloping flux return structure into rings to limit the formation of eddy currents. Conventionally, the rings are arranged separately from each other and completely electrically separated from each other by insulating layers. In the case of the micromotor according to the invention, the rings are not completely separated from each other, the bridges, however, which are only arranged at some locations of the periphery, do not lead to the formation of substantial eddy currents. Consequently, the entire enveloping flux return structure can be made of a continuous body. The enveloping flux return structure can have a wall thickness of 0.2–0.4 mm, i.e., an extremely small wall thickness, the bridges interconnecting the rings providing the required cohesion and the necessary strength. Due to the small wall thickness of the enveloping flux return structure, it may occur that the enveloping flux return structure is operated in magnetic saturation without being able to receive the entire magnetic flux. The micromotor according to the invention has a rotational speed of at least 30,000 revolutions per minute and typically of 60,000 revolutions per minute. The enveloping flux return structure has the required structural strength required for the assembly as well as for the operation of the micromotor. If thin lamellae were glued together, such a structural strength could not be achieved.

According to a preferred development of the invention, the bridges of the enveloping flux return structure form a longitudinal continuous web. This means that the bridges are oriented relative to each other. This orientation can be effected along a line parallel to the motor axis or preferably along a helical line. Preferably, there are at least two webs which are distributed around the circumference.

According to a preferred development of the invention, the enveloping flux return structure integrally passes into a pump housing. The enveloping flux return structure divided into rings in the region of the micromotor is continuous in the region of the pump housing. Because of the integrity of pump housing and enveloping flux return structure, a particularly exact centering of the pump housing relative to the micromotor is achieved. The assembly and the demands of precision made thereon are simplified.

Further, the invention relates to a method of manufacturing a micromotor. In this method, the enveloping flux return structure of the micromotor is manufactured of a ferromagnetic tube by laser cutting, in the course of which peripheral slots interrupted by bridges are generated. Hereinafter, an embodiment of the invention is explained in detail with respect to the drawings.

In the Figures:

FIG. 1 is a side view of a pump with micromotor,

FIG. 2 is a longitudinal cross-sectional view of FIG. 1, and

Figure 3:
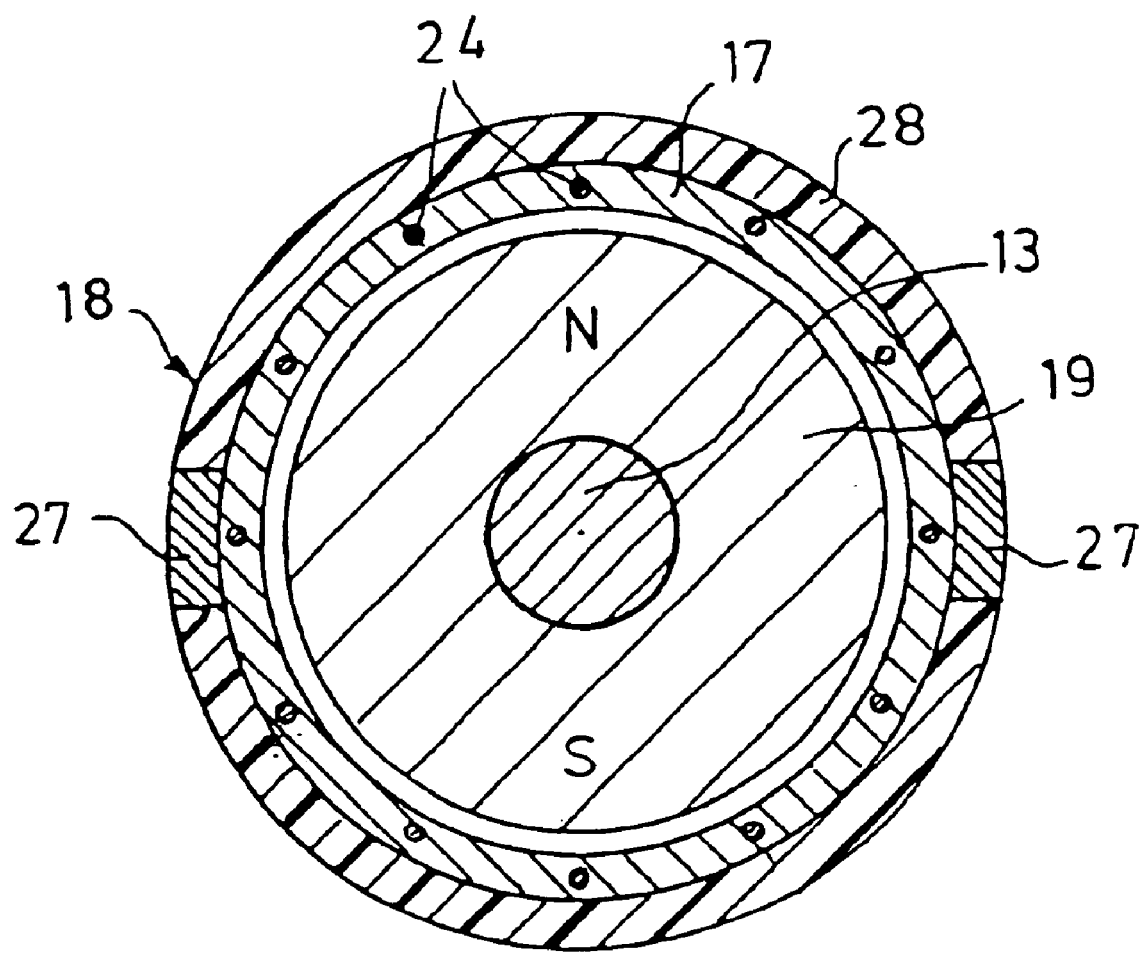
FIG. 3 shows a cross-section along the line III—III of FIG. 2.

The pump illustrated in the figures comprises a micromotor 10 axially followed by a pump portion 11. The pump portion 11 comprises an impeller 12 mounted on a shaft 13 and rotating in a tubular pump housing 14.

The micromotor 10 includes a stator 15 and a rotor 16 connected to the shaft 13. The stator 15 consists of a tubular sleeve 17 and an enveloping flux return structure 18 closely surrounding the sleeve 17. The rotor 16 includes a magnet 19 whose north pole N and south pole 1 are arranged at diametrically opposed locations of the periphery. The magnet 19 is fastened on the shaft 13. At the rear end, the shaft 13 is supported in the sleeve 17 by means of a ball bearing 20 and at the front end facing the impeller 12, it is supported in a sealing bearing 21.

The rear end of the stator 15 is followed by a transition piece 22 adapted to be connected to a catheter (not illustrated). Wires 23 connected to an excitation winding 24 in the interior of the sleeve extend through the transition piece 22. The excitation winding 24 is flown through by an externally controlled alternating current the frequency of which determines the rotational speed of the motor. The sleeve 17 including the excitation winding 24 consists of a plastic layer with embedded wires and a thickness of about 0.2 mm. The wires are wound in two layers corresponding to a given configuration. Between the stator 15 and the rotor 16, there is a narrow gap in the dimensional range of one tenth of a millimeter.

The enveloping flux return structure 18 consists of an integral tubular body into which circumferential slots 25 are cut. The slots 25 define respective rings 35. Each slot 25 extends over less than 360°. In the present case, each slot is interrupted by two diametrically opposed bridges 26. The bridges 26 of adjacent slots form a longitudinal continuous web 27. Here, this web extends helically. A corresponding web 27 is located on the opposite side not illustrated in FIG. 1.

The slots 25 connecting adjacent rings 35 are made by laser-cutting of a ferromagnetic tube, the cutting width being less than a tenth of a millimeter, particularly about 0.05 mm. Generally, the number of slots 25 should be as great as possible so that the rings are as narrow as possible. Preferably, the width of the rings is 0.2–0.3 mm.

The slots 25 are filled up with plastic material 28 (FIG. 3), resulting in a continuous smooth outer surface of the enveloping flux return structure 18. At the same time, the enveloping flux return structure 18 forms the outer skin of the micromotor. If necessary, it can be coated with an additional plastic layer.

As shown in FIG. 3, the slots 25 filled with the plastic material 28 extend through the entire thickness of the enveloping flux return structure. The enveloping flux return structure 18 closely surrounds the sleeve 17 containing the excitation winding 24.

The wall thickness of the enveloping flux return structure amounts to about 0.25 mm, the outer diameter amounts to 4 mm and the inner diameter 3.45 mm. The length of the enveloping flux return structure 18 is 12 mm.

The enveloping flux return structure 18 is continued by webs 30 forwardly projecting from the front end of the micromotor and integrally passing into the wall of the pump housing 14. Therefore, the pump housing 14 is integrally formed with the enveloping flux return structure 18 and consists of the same material. This means that the pump housing 14 has the same outer diameter and the same inner diameter as the enveloping flux return structure 18. In the present embodiment, the webs 30 do not extend parallel to the axis of the micromotor, but helically, in correspondence with the course of the flow generated by the helical impeller 12. When the pump housing is formed integrally with the enveloping flux return structure, the wall thickness in the region of the pump housing is alternatively smaller than in the region of the enveloping flux return structure. Thus, a uniform tube can be provided the inner diameter of which is made larger in the region of the pump housing than in the region of the enveloping flux return structure by drilling or boring, while the outer diameter is the same all over.

The openings 31 formed between the webs 30 form the outlets of the pump and the end opening 32 of the pump housing 14 forms the inlet of the pump. The pump can also be driven in opposite direction so that the openings 31 form the inlet and the opening 32 forms the outlet.

What is claimed is:

1. A micromotor comprising a stator including a sleeve with an excitation winding and an enveloping flux return structure, wherein said enveloping return structure comprises an integral body formed from a single piece of sheet metal having spaced ferromagnetic rings wherein adjacent rings are connected by at least one bridge.

2. The micromotor of claim 1, wherein said at least one bridge forms a continuous web along said enveloping flux return structure.

3. The micromotor of claim 1, wherein a pump housing comprises an integral portion of said enveloping flux return structure.

4. The micromotor of claim 3, wherein spaces between said spaced ferromagnetic rings are filled with a plastic material and said enveloping flux return structure forms an outer wall of a motor housing.

5. The micromotor of claim 3, wherein said enveloping flux return structure has an outer diameter of not more than 4 mm and an inner diameter least 3.3 mm.

6. The micromotor of claim 2, wherein a pump housing comprises an integral portion of said enveloping flux return structure.

7. The micromotor of claim w, herein spaces between said spaced ferromagnetic rings are filled with a plastic material and said enveloping flux return structure forms an outer wall of a motor housing.

8. The micromotor of claim 6, wherein said continuous web defines a helix.

9. The micromotor of claim 2, wherein spaces between said spaced ferromagnetic rings are filled with a plastic material and said enveloping flux return structure forms an outer wall of a motor housing.

10. The micromotor of claim 9, wherein said continuous web defines a helix.

11. The micromotor of claim 1, wherein spaces between said spaced ferromagnetic rings are filled with a plastic material and said enveloping flux return structure forms an outer wall of a motor housing.

12. The micromotor of claim 11, wherein said enveloping flux return structure has an outer diameter of not more than 4 mm and an inner diameter of at least 3.3 mm.

13. The micromotor of claim 1, wherein said enveloping flux return structure has an outer diameter of not more than 4 mm and an inner diameter of at least 3.3 mm.

* * * * *